(12) United States Patent
Newman et al.

(10) Patent No.: US 8,214,006 B2
(45) Date of Patent: Jul. 3, 2012

(54) DEVICES AND METHODS FOR DETECTING β-HAEMATIN AND HAEMOZOIN

(75) Inventors: David Michael Newman, Teignmouth (GB); John Heptinstall, Kenilworth (GB)

(73) Assignees: Coventry University, Coventry (GB); University of Exeter, Exeter (GB)

( * ) Notice: Subject to any disclaimer, the term of this patent is extended or adjusted under 35 U.S.C. 154(b) by 552 days.

(21) Appl. No.: 12/513,990

(22) PCT Filed: Nov. 9, 2007

(86) PCT No.: PCT/GB2007/004300
§ 371 (c)(1),
(2), (4) Date: May 7, 2009

(87) PCT Pub. No.: WO2008/056171
PCT Pub. Date: May 15, 2008

(65) Prior Publication Data
US 2009/0318784 A1  Dec. 24, 2009

(30) Foreign Application Priority Data
Nov. 10, 2006 (GB) .................. 0622450.5

(51) Int. Cl.
*A61B 5/1455* (2006.01)
*G01N 21/00* (2006.01)
(52) U.S. Cl. .............. 600/322; 422/82.05; 356/39
(58) Field of Classification Search .......... 600/309, 600/310, 322; 324/201
See application file for complete search history.

(56) References Cited

U.S. PATENT DOCUMENTS
5,978,694 A * 11/1999 Rapoport ............... 600/309
6,636,752 B1 * 10/2003 Madarasz et al. ......... 600/310
(Continued)

FOREIGN PATENT DOCUMENTS
JP  55 024614  2/1980
(Continued)

OTHER PUBLICATIONS

Moore et al., "Hemoglobin degredation in malaria-infected erythrocytes determined from live cell magnetophoresis", The FASEB Journal, express article 10.1096/fj.05-5122fje, 19 pages, Feb. 6, 2006.*

(Continued)

*Primary Examiner* — Eric Winakur
(74) *Attorney, Agent, or Firm* — King & Schickli, PLLC (57) ABSTRACT

In the application, the change in the magnetic state of the haemoglobin caused by the malarial infection is exploited by detecting suitable properties of haemozoin which are dependent on the application of a magnetic field. FIG. 1 shows apparatus, shown generally at (10), for performing magneto-optical detection using photo-acoustic techniques. The apparatus (10) comprises a light source (12), producing a beam of optical radiation (14) which passes through a polarizer (16), a variable LC retarder (0 or 180° retardance) (18), and a (chopper 20), before impinging on a sample (22) held in a sample holder (24). The sample is in direct contact with an acoustic detector (26). The apparatus (10) further comprises an electromagnet (28), and a Gauss meter (30) can be utilized to measure the applied magnetic field strength. Advantages associated with this approach are the—possibility of making in vivo measurements, and the avoidance of problems of optical scattering associated with conventional optical measurements on turbid liquids such as whole blood.

19 Claims, 9 Drawing Sheets

U.S. PATENT DOCUMENTS

2001/0028031 A1    10/2001    Engelhardt et al.
2006/0025659 A1    2/2006    Kiguchi et al.

FOREIGN PATENT DOCUMENTS

WO    WO 02/16910    2/2002
WO    WO 03/029790    4/2003

OTHER PUBLICATIONS

Balasubramanian et al; "The malaria parasite monitored by photoacoustic spectroscopy"; Science, vol. 223, No. 4638, 1984, pp. 828-830, XP002475730, ISSN: 0036-8075.

Nalbandian et al; "A Molecular-based Magnet Test for Malaria"; American Journal of Clinical Pathology, vol. 103, No. 1, 1995, pp. 57-64, XP009098407, ISSN:0002-9173.

Sullivan et al; "Haemozoin: Identification and quantification"; Parasitology Today, vol. 12, No. 4, 1996, pp. 161-163, XP002475729, ISSN: 0169-4758.

Carey et al; "Photo-acoustic detection of magneto-optic absorption (MPAS) in thin iron films"; Journal of Physics D. Applied Physics, vol. 15, No. 2, Feb. 14, 1982, pp. 343-346, XP020012191, ISSN: 0022-3727.

* cited by examiner

+/- 14kOe
0.1 ml of 20μg/ml solution

DEVICES AND METHODS FOR DETECTING β-HAEMATIN AND HAEMOZOIN

FIELD OF THE INVENTION

This invention relates to devices and methods for the detection of β-haematin and haemozoin, with particular, but by no means exclusive, reference to the detection of malaria.

BACKGROUND OF THE INVENTION

Malaria remains a major health problem in many parts of the world. In regions where it is endemic, effective treatment and eradication is often compromised by lack of access to rapid, accurate and affordable diagnosis since, unfortunately, the best diagnostic tools currently available require a laboratory environment. Even in Europe the number of cases and fatalities increases year on year reflecting the increasing preference of Europeans to holiday in malarial prevalent areas coupled with a reluctance to take anti-malarial prophylaxes. Native Europeans have no immunity so that without early diagnosis infection can, and often does, have rapidly fatal consequences. This situation is moreover only likely to worsen as global warming is now predicted to facilitate the spread of malaria to areas previously free of the disease including southern Europe.

SUMMARY OF THE INVENTION

Examination by high-power microscopy, typically of 100 fields of Giemsa-stained thick blood smears, is still generally regarded as the so called "gold standard" for malarial diagnosis. Dominant for more than a century, this technique can in principle attain a sensitivity of 5 to 20 parasite infected cells per µl of blood. It is however time consuming and in reality subject to significant variability in its application, particularly in respect of the number of fields examined and the methodology employed to determine parasitaemia from parasite counts within the fields examined. Coupled with its dependence on the skill base of highly trained microscopists, the sensitivity discussed above is consequently rarely obtained outside specialist laboratories. Recognition of this and of the need for more rapid diagnosis has over the last decade or so driven the study and development of several alternative techniques. Fluorescent microscopy, laser desorption mass spectrometry and techniques involving PCR amplification to detect and identify nucleic acid sequences are currently acknowledged as the most sensitive and specific techniques available. However, in general this emerging generation of diagnostic procedures remains time consuming and again too costly and complex for dissemination beyond specialist laboratories. For field application rapid detection tests (RDTs), in the form of sensor sticks or wands, are now available from a variety of manufacturers. These employ immuno-chromatographic methods to detect malarial antigens such as the histidine-rich protein II (HRP-II) and/or parasite lactate dehydrogenase (pLDH) which are present in peripheral blood during infection. These tests generate results within 15 minutes and require only minimal operator training. However, they are relatively expensive, non-quantitative and have a limited usefulness in detecting low level parasitaemia (<100 parasites/µl). There is still a pressing need for new diagnostic techniques affording rapid yet simpler to operate instrumentation. Furthermore, there is a need for such a technique which is quantitative. Furtherstill, there is a need for a device for detecting malaria which is suitable for field use or first point symptom presentation.

The present invention, in at least some of its embodiments, addresses the above described problems and needs.

According to a first aspect of the invention there is provided a method of detecting the presence of an analyte in a sample, in which the analyte is haemozoin, β-haematin or an analogous iron containing compound, the method including the steps of:
providing the sample;
applying a magnetic field across at least a portion of the sample;
detecting a physical property of the sample, the detected physical property corresponding to a physical property of the analyte which varies in dependence with an applied magnetic field; and
correlating the detected physical property with the presence of the analyte.

The term 'analogous iron containing compound' is understood to mean a compound having substantially identical spectroscopic, magnetic and crystallographic properties and characteristics to haemozoin and β-haematin.

The detection of the physical property of the sample may include the step of introducing electromagnetic radiation into the sample. Preferably the physical property is a property associated with the absorption of the electromagnetic radiation. Advantageously, a magneto-optical spectroscopic detection technique is utilised. Accordingly, the electromagnetic radiation may be in the range 400 to 700 nm. Preferably the electromagnetic radiation is greater than 600 nm and most preferably is in the range 640 to 680 nm. It may be possible to utilise electromagnetic radiation of other wavelengths. For example, ultraviolet radiation or near infra-red radiation, especially in the 700-900 nm region, might be used.

Advantageously, the electromagnetic radiation is polarised. The polarisation state of the electromagnetic radiation may be varied, and the presence of the analyte detected by detecting a dependence of the detected physical property on the polarisation state.

In preferred embodiments the transmission of the electromagnetic radiation through the sample or the generation of photo-acoustic energy is detected.

The detected physical property may be associated with a non-linear wave mixing process. In particular, radiation produced by second harmonic generation may be detected.

The detected physical property may be the generation of surface plasmons, said generation being augmented by the presence of the analyte and varying in dependence with the applied magnetic field.

Alternatively, the detected physical property may be the specific heat of the sample, the thermal conductivity of the sample, or a property associated with the transmission of ultrasound through the sample, such as the intensity of ultrasound transmission through the sample.

In some embodiments the magnitude and/or the direction of the applied magnetic field is varied, and the presence of the analyte is detected by detecting a dependence of the detected physical property on the variation of the applied magnetic field. For the avoidance of doubt, said variation of the applied magnetic field includes embodiments in which measurements are made with and without an applied magnetic field.

Phase sensitive detection of the physical property may be performed using modulation of the applied magnetic field and/or the electromagnetic radiation introduced into the sample.

According to a second aspect of the invention there is provided a method of detecting the presence of malarial parasites in a blood containing sample including the steps of:

detecting the presence of haemozoin in the blood containing sample by a detection technique which is substantially unaffected by the presence of other constituents of the blood;

correlating the presence of haemozoin with the presence of malarial parasites in the blood containing sample.

The step of detecting the presence of haemozoin may be performed ex vivo or in vivo.

Preferably, the step of detecting the presence of haemozoin is performed by applying a magnetic field across at least a portion of the blood containing sample and detecting a physical property of the blood containing sample, the detected physical property corresponding to a physical property of haemozoin which varies in dependence with an applied magnetic field. Alternatively, it may be possible to detect haemozoin without applying a magnetic field, for example using a spectroscopic technique. It will be apparent that the first aspect of the invention can be used to detect the presence of haemozoin.

According to a third aspect of the invention there is provided a device for detecting the presence of an analyte in a sample, in which the analyte is haemozoin, β-haematin or an analogous iron containing compound, the device including:

magnetic field applying means for applying a magnetic field across at least a portion of the sample;

detection means for detecting a physical property of the sample, the detected physical property corresponding to a physical property of the analyte which varies in dependence with an applied magnetic field; and correlation means for correlating the detected physical property with the presence of the analyte.

According to a fourth aspect of the invention there is provided a device for detecting the presence of malarial parasites in a blood containing sample including:

means for detecting the presence of haemozoin in the blood containing sample, the detection being substantially unaffected by the presence of other constituents of the blood; and means for correlating the presence of haemozoin with the presence of malarial parasites in the blood containing sample.

Preferably, the means for detecting the presence of haemozoin includes magnetic field applying means for applying a magnetic field across at least a portion of the sample and detection means for detecting a physical property of the sample, the detected physical property corresponding to a physical property of haemozoin which varies in dependence with an applied magnetic field.

The magnetic field applying means may include a permanent magnet.

The magnetic field applying means may be controllable so as to vary the magnitude and/or the direction of the applied magnetic field. The magnetic field applying means may be an electromagnet.

The magnetic field applying means may include micro-magnetic elements. In general, the micro-magnetic elements are of dimensions comparable to the crystal length of the analyte, typically around 1-2 µm. The micro-magnetic elements may comprise pole pieces of a suitable material, such as soft nickel or NiFe. Typically the micro-magnetic elements are embedded in a substrate formed from an optically inert substrate which does not exhibit birefringence or dichroisn.

The detection means may include means for providing electromagnetic radiation and sensing means for detecting a physical property associated with the absorption of the electromagnetic radiation by haemozoin. The means for providing electromagnetic radiation may provide polarised electromagnetic radiation. Alternatively, unpolarised radiation may be provided. The wavelength of the electromagnetic radiation may be in the range 400 to 700 nm, preferably greater than 600 nm and most preferably in the range 640 to 680 nm.

The sensing means may be an acoustic detector.

The sensing means may be an electromagnetic radiation detector for detecting electromagnetic radiation transmitted through the sample.

The detection means may include means for varying the intensity of the electromagnetic radiation and means for detecting a dependence of the physical property on the variation of said intensity.

The presence of haemozoin may be detected by varying the magnitude and/or the direction of the applied magnetic field.

Phase sensitive detection means may be employed.

The polarisation state of the polarised electromagnetic radiation may be controllably variable. In these embodiments the presence of haemozoin may be detected by varying the polarisation state of the polarised electromagnetic radiation and observing a polarisation state dependence in the detected physical property. The means for providing electromagnetic radiation may provide pulsed, polarised electromagnetic radiation, and the sensing means may include means for separating ballistic and quasi-ballistic photons from diffuse photons. A gating system may be used for this purpose. In this way the effects depolarisation occurring within the patient's tissue can be countered.

The means for providing polarised electromagnetic radiation may include at least one laser. The means for providing polarised electromagnetic radiation may include at least a pair of lasers, in which the first laser in the pair produces a first beam of electromagnetic radiation and the second laser in the pair produces a second beam of electromagnetic radiation, and wherein the first and second beams have differing, preferably orthogonal, polarisation states when introduced into the sample.

The first and second beams may be combined using an optical element so that the beams are co-linear when introduced into the sample.

The first and second beams of electromagnetic radiation may be intensity modulated 180° out of phase.

Preferably, each laser in the pair has an electronic driving arrangement which controls the production of the respective beams of electromagnetic radiation, and the device further includes control means for controlling the electronic driving arrangements so that the first and second beams of electromagnetic radiation are intensity modulated 180° out of phase.

The device may be configured so that the electromagnetic radiation propagates into the sample along an axis, and the magnetic field applying means applies a magnetic field which is aligned in parallel with said axis of propagation.

Alternatively, the device may be configured so that the electromagnetic radiation propagates into the sample along an axis, and the magnetic field applying means applies a magnetic field which is aligned orthogonal to said axis of propagation.

In preferred embodiments, the device is attachable to peripheral tissue of a patient, preferably an ear lobe or a finger, and the means for detecting the presence of haemozoin performs in vivo detection of the presence of haemozoin in the bloodstream of the patient.

According to a fifth aspect of the invention there is provided a device for producing a beam of polarisation modulated electromagnetic radiation including a first laser producing a first beam of electromagnetic radiation, a second laser producing a second beam of electromagnetic radiation, a first polarising arrangement for polarising the first beam of electromagnetic radiation, a second polarising arrangement for polarising the second beam of electromagnetic radiation, in which the first and second polarising arrangements are configured so that the first and second beams are polarised with orthogonal polarisation states, an optical element for combining the polarised beams so that said beams are co-linear, and intensity modulation means for intensity modulating the intensities of the first and second beams.

This arrangement has been found to be with a highly advantageous way of producing an intensity modulated beam of orthogonal polarisation states. The device can be applied advantageously to the detection techniques discussed herein. However, the device may be usefully applied to other investigative techniques or experiments which require a source of electromagnetic radiation which alternates between orthogonal polarisation states.

Preferably, the lasers are semiconductor lasers.

Preferably, the first and second beams of electromagnetic radiation are intensity modulated 180° out of phase. Advantageously, the first and second lasers each have an electronic driving arrangement which controls the production of its respective beam of electromagnetic radiation, and the device further includes control means for controlling the electronic driving arrangements so that the first and second beams of electromagnetic radiation are intensity modulated 180° out of phase. The control means may include a digital clock producing a digital clock signal, and means for converting the digital clock signal into two out of phase digital clock signals such that each laser is alternately switched between two intensity levels, the switching of the first laser being 180° out of phase with the switching of the second laser.

The optical element for combining the beams may be a polarising beams splitter.

At lease one of the first and second beams may be directed by a polarising beam splitter to the optical element which combines the beams.

Prior to being combined by the optical element, each of the first and second beams may be polarised using separate Glan Taylor polarisers.

At least one of the polarising arrangements may include an adjustment stage for controllably adjusting the polarisation state of the first or second beam. The adjustment stage may be a rotary stage which controllably rotates at least one element of a polarising arrangement.

BRIEF DESCRIPTION OF THE DRAWING FIGURES

Whilst the invention has been described above, it extends to any inventive combination or sub-combination of the features set out above or in the following description or drawings or claims.

Embodiments of methods and devices in accordance with the invention will now be described with reference to the accompanying drawings, in which:—

FIG. 1 shows (a) a first arrangement and (b) a second arrangement of a device of the invention;

FIG. 5 shows (a) the results of further experiments measuring differential transmittance against the concentration of β-haematin in blood and (b) the results of experiments measuring differential transmittance against the concentration of haemazoin in blood;

FIG. 8 shows device for making in vivo measurements of malaria infection which are attached to (a) an ear lobe and (b) a finger tip;

DETAILED DESCRIPTION OF THE INVENTION

Although the present invention is applicable to the detection of haemozoin and β-haematin per se, an important aspect of the invention relates to the detection of the malarial parasite. The malarial parasite enters the red blood cells (erythrocytes) and converts the haemoglobin to haemozoin, which changes the magnetic state in the process. The erythrocytes subsequently burst, releasing haemozoin into the plasma, whilst the malarial parasite goes on to infect further erythrocytes. The present inventors have realised that it may be possible to detect the malarial parasite by detecting the presence of haemozoin in the blood.

In particularly preferred embodiments, the change in the magnetic state of the haemoglobin caused by the malarial infection is exploited by detecting suitable properties of haemozoin which are dependent on the application of a magnetic field.

Figure 1A:
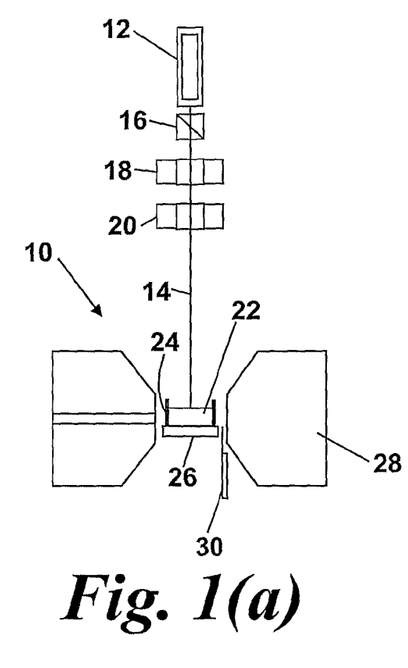
Figure 1B:
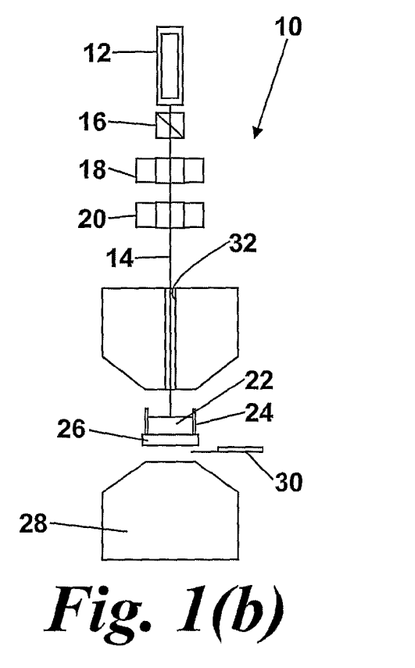
Figure 2:
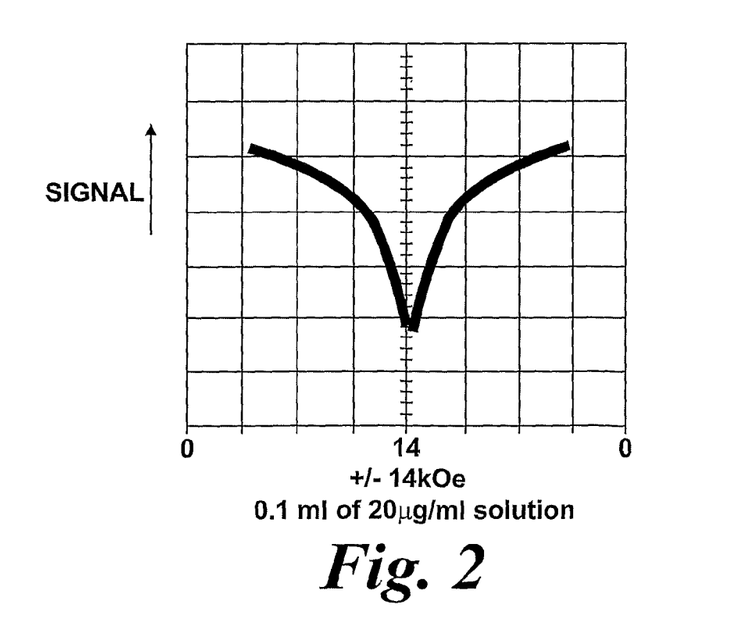
FIG. 2 shows observed signals of a function of applied magnetic fields.

In one preferred embodiment, photo-acoustic detection is used. Advantages associated with this approach are the possibility of making in vivo measurements, and the avoidance of problems of optical scattering associated with conventional optical measurements on turbid liquids such as whole blood. FIG. 1 shows apparatus, shown generally at 10, for performing magneto-optical detection using photo-acoustic techniques. The apparatus 10 comprises a light source 12, producing a beam of optical radiation 14 which passes through a polariser 16, a variable LC retarder (0 or 180° retardance) 18, and a chopper 20, before impinging on a sample 22 held in a sample holder 24. The sample is in direct contact with an acoustic detector 26. The apparatus 10 further comprises an electromagnet 28, and a Gauss meter 30 can be utilised to measure the applied magnetic field strength. In the arrangement shown in FIG. 1a, the electromagnet 28 is arranged orthogonal to the axis of the beam 14. In the arrangement shown in FIG. 1b, the electromagnet 28 is arranged parallel to the axis of the beam 14, and a bore 32 is provided in the electromagnet 28 allowing the beam to travel to the sample 22. It will be apparent to the skilled reader that in the arrangement shown in FIG. 1a the applied magnetic field is orthogonal to the axis of the beam 14, whereas in FIG. 1b, the applied magnetic field is parallel to the axis of the beam 14. Typically the light source 12 is a laser of any suitable type, and in one set of experiments a semiconductor laser operating at 650 nm is utilised. Experiments were performed using laser light which is polarised in the plane of the paper of FIG. 1 (henceforth termed p polarisation) and laser radiation polarised out of the plane of the paper (henceforth termed s polarisation). Experiments were performed on solutions of the haemozoin analogue β-haematin. With the arrangement shown in FIG. 1a, i.e., with the magnetic field applied parallel to the plane of the sample 22, the recorded signal follows an $M^2$ relationship with the field. The signal decreases upon applied field for p polarisation and increases for s polarisation. When the arrangement shown in FIG. 1b is employed, i.e., when the field is applied perpendicular to the plane of the sample 22, the signal is also $M^2$ in nature but increases with magnetic field irrespective of the polarisation state. FIG. 2 shows a signal obtained using the arrangement shown in FIG. 1a and laser radiation having p polarisation in an experiment in which the magnetic field was ramped from 0 to 14 kOe and then ramped down to 0 kOe. It can be seen that the signal decreases with increasing field strength.

Without wishing to be bound or otherwise limited by any particular theory, it is believed that the results discussed above can be explained as follows. Crystals of β-haematin are rod shaped. On excitation with linearly polarised radiation, the crystals of β-haematin absorb when the electric vector of the radiation is along the axis of the rod. In suspension in blood or other fluid the axes of the β-haematin crystals are randomly orientated and so the suspension expresses no preferred direction absorption on interrogation using linearly polarised radiation. However, on application of a magnetic field the crystals behave simply as weak bar magnets experiencing a torque that seeks to orient them along the applied field direction. This is opposed by the thermal energy of their environment that constantly acts to randomise the assembly. The experiments show that the crystals can be held in close alignment on application of fields around 14 kOe. In the arrangement shown in FIG. 1a, differential absorptive signals which are characteristic of the presence of β-haematin can be obtained by switching the polarisation state of the optical radiation from parallel to the applied field direction to orthogonal to the applied field direction. Alternatively, the same measurement can be made by reversing the magnetic field along a direction orthogonal to the polarisation direction of the light wave. It will be apparent to the skilled reader that the arrangement shown in FIG. 1b is not suitable for this differential absorption detection technique, since p and s polarised light produced the same results. However, it is possible to detect β-haematin using the FIG. 1b arrangement by varying the magnitude of the magnetic field whilst interrogating the sample with linearly polarised radiation, and monitoring the dependence of the signal on the magnetic field. This approach can also be utilised with the FIG. 1a arrangement.

Figure 3:
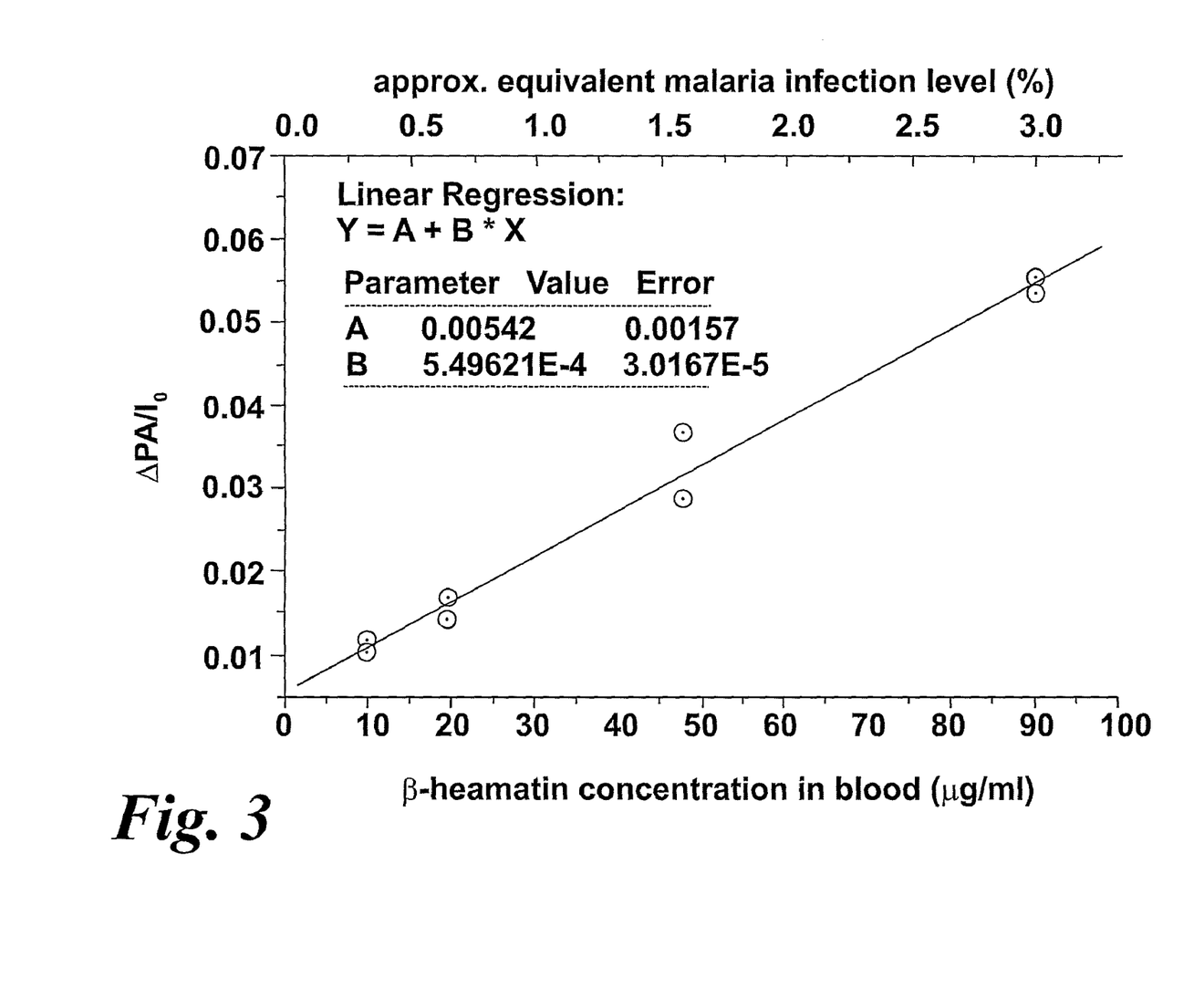
FIG. 3 shows differential absorptive signal against the concentration of β-haematin in blood.

Experiments have been performed interrogating samples of β-haematin in human blood. The FIG. 1a arrangement was utilised and the difference between the signals obtained with p and s polarised light were investigated, i.e., a differential absorptive signal was obtained. FIG. 3 shows a differential absorptive signal (designated as $\Delta PA/I_0$) against the β-haematin concentration in blood. As can be seen in FIG. 3, it has been established that the presence of β-haematin in blood is readily detectable at levels at less than 10 μgm/ml. This is broadly equivalent to a malarial infection or parasitemia level of 0.3%. However, it should be noted that at this concentration both the signal level and the signal noise ratio are such that previous experience allows confident expectation that the detectivity of the technique can be extended down to parasitemia levels of 0.05% or more. The limitation to calibration of parasitemia levels significantly below 0.3% is merely constrained by the difficulty of creating 0.1 ml samples containing β-haematin uniformly dispersed at concentrations less than 10 μgm/ml.

Experiments were performed on β-haematin because it is a close analogue of haemozoin. For example, electron micrographs of β-haematin and haemozoin reveal a near identical rod-like crystal morphology. Furthermore, S. Pagola et al, Nature 404, 2000 and references therein state that "β-haematin is chemically, spectroscopically and crystallographically identical to haemozoin". It is thus envisaged that results obtained using β-haematin should be transposable to measurements on harvested malarial blood containing haemozoin.

Although the photo-acoustic experiments discussed above were performed at 650 mn, light of other wavelengths may be utilised. In particular, it may be possible to utilise light of shorter wavelengths, for example in the blue/green region of spectrum.

Figure 4:
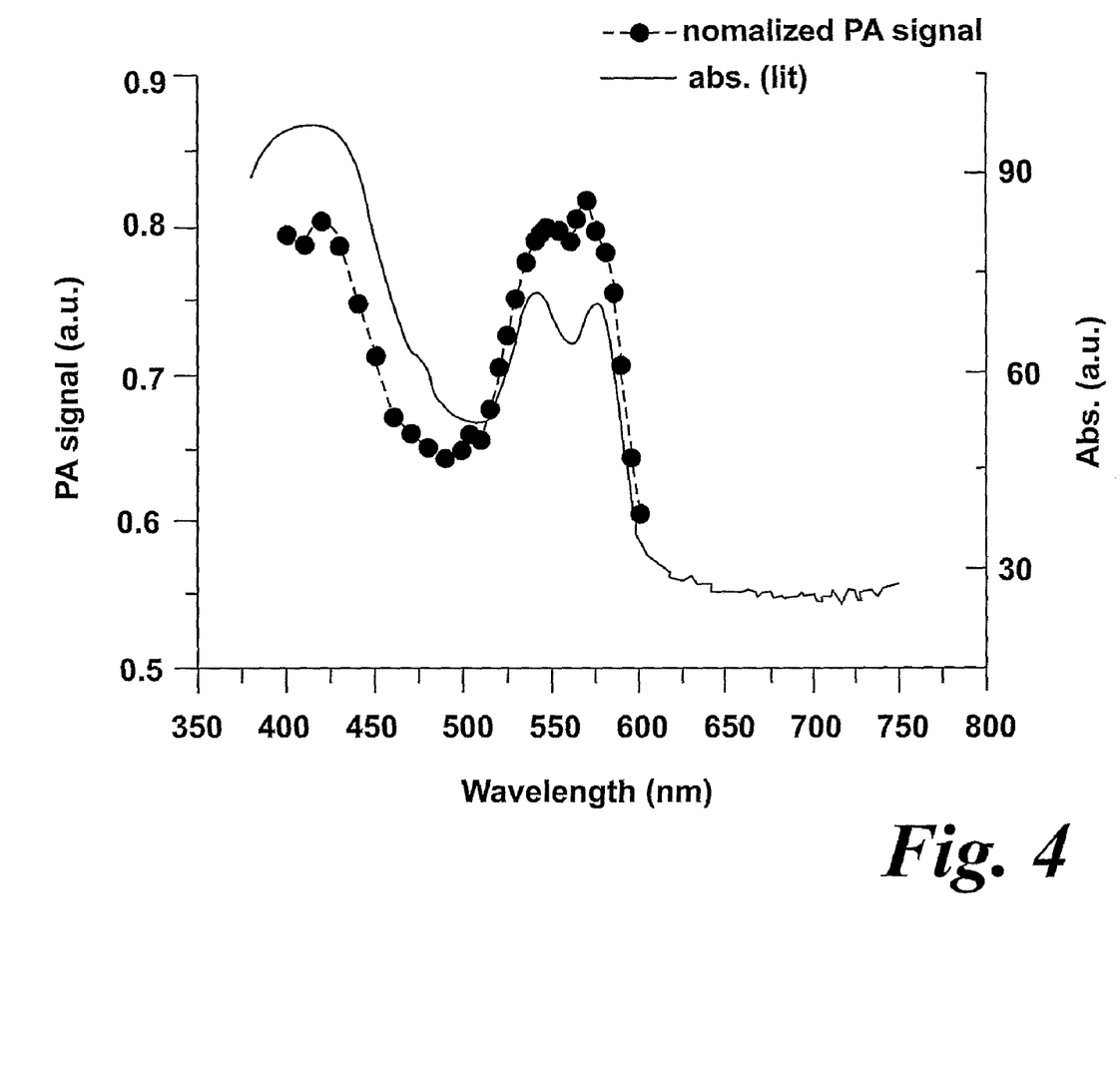
FIG. 4 shows the absorption spectrum of whole blood.

In another preferred embodiment, it has been found that it possible to detect β-haematin in blood using optical transmission detection. FIG. 4 shows the absorption spectrum for whole blood. It can be seen that above 600 nm blood absorbs much less strongly. The present inventors have realised that β-haematin absorbs significantly above 600 nm, and in fact a peak is seen in the absorption spectrum of β-haematin at 659 nm. Furthermore, it appears that scattering from whole blood at wavelengths above 600 nm is at least a manageable concern. Thus, the detection of β-haematin can be accomplished using arrangements which are very similar to the arrangements shown in FIGS. 1a and 1b, with the exception that the photo-acoustic detector is replaced with an optical detector such as a silicon photo detector. Experiments were performed at 650 nm using a semiconductor laser light source to interrogate β-haematin in blood, and very similar results to those shown in FIG. 3 were obtained using the differential absorptive signal approach to look at the differences between optical transmission using p and s polarised light.

β-haematin in blood was interrogated also with a very similar experimental set-up in which 660 nm light from a semiconductor laser is used in conjunction with a photodetector to measure transmission through blood samples. A 1 T in plane magnetic field was utilised. The results are presented in FIG. 5, which demonstrate that measurable differential signals are observed in connection with β-haematin concentrations down to the 1 μg/ml level or lower.

It was originally envisaged that late stage malarial infection (in which the erythrocytes have broken down, releasing free haemozoin into the plasma) can be readily detected using the techniques discussed above. Early stage infection, in which the haemozoin is still confined within the erythrocytes, was originally envisaged to be detectable, although it was not originally clear whether haemozoin which is still confined in the erythrocytes is fully mobile and free to rotate. It is possible that the presence of the erythrocytes will slow down the alignment of the haemazoin with the magnetic field, in which case a different response might be obtained that are obtained with free haemozoin in blood plasma. Alternating magnetic fields might be utilised in order to identify early stage infection, and to separate and independently evaluate the response of haemozoin in the plasma from that of haemozoin in the erythrocytes. For example, the response may be characteristically dependent on the frequency of the alternating magnetic field. These considerations are principally of relevance to in vivo detection. With ex vivo detection, for example using a device that analyses a pinprick of blood, it is possible to lyaise the red cells, for example by adding a small amount of detergent to the sample or for injecting the cells to a freeze thaw cycle.

Further experiments have confirmed that both later and early stage malarial injection can be detected.

In one set of experiments, fresh blood was doped with varying concentrates of haemazoin in the form of mature trophozoite stage parasitized red blood cells (PRBCs) grown in culture and lysed by freezing and thawing before diluting with the whole fresh blood. The samples were analysed using the experimental set-up employed to obtain the data shown in FIG. 5a, ie, the fractional change in transmittance at 660 nm was measured. The results of the measurements on blood doped with haemazoin are shown in FIG. 5b.

The linearity of the plots shown in FIGS. 5a and 5b is striking and continues unshown out to concentrations beyond at least 100 µg/ml. Note also how the data point (■),obtained with cells in which the infection is at the early ring stage of hemozoin formation when the crystals are believed to be much smaller, fits closely to the linear trend. The difference in the gradients of the two plots may be a consequence of at least two factors. Firstly, haemozoin crystals in situ exhibit a tendency to clump, which would reduce the dichroism when compared with an equivalent number of individual crystals, such as is the case with β-haematin. Secondly, cultured cells are supplied frozen to ensure all cells are at the same point in their infection cycle and to facilitate safe handling. Freezing however appears to only partially release the haemozoin so that cellular debris continues to adhere to the crystals, altering the dynamical forces acting upon them and possibly constraining the rotation achieved in a given applied field. Adherence of diamagnetic cellular material to the crystals might for example result in a small torque opposing that seeking to orientate the crystals with the field. Alternatively, adhering cellular material might simply be providing a larger interaction cross-section for the thermal restoring mechanism. Plots obtained in the same way as FIG. 5a for blood doped in this manner have exactly the same form but with reduced dichroism. Similarly, the rate of response of the dichroic signal to changes in the applied field is also observed to be reduced. It may be preferable in practice to use a detergent to completely release the haemozoin in order to restore the dichroic signal strength to that exhibited by an equivalent β-haematin concentration. The effectiveness of this procedure has been tested by extracting the haemozoin from two samples of parasitized red blood cells (PRBCs) used in producing FIG. 5b. This is cleaned before reintroducing it at the same concentration into whole fresh blood. The fractional intensity change for these samples is plotted as (◇) in FIG. 5a. It can be seen that the haemozoin samples treated is this way provide results which are in very close agreement with the β-haematin results.

Figure 5:
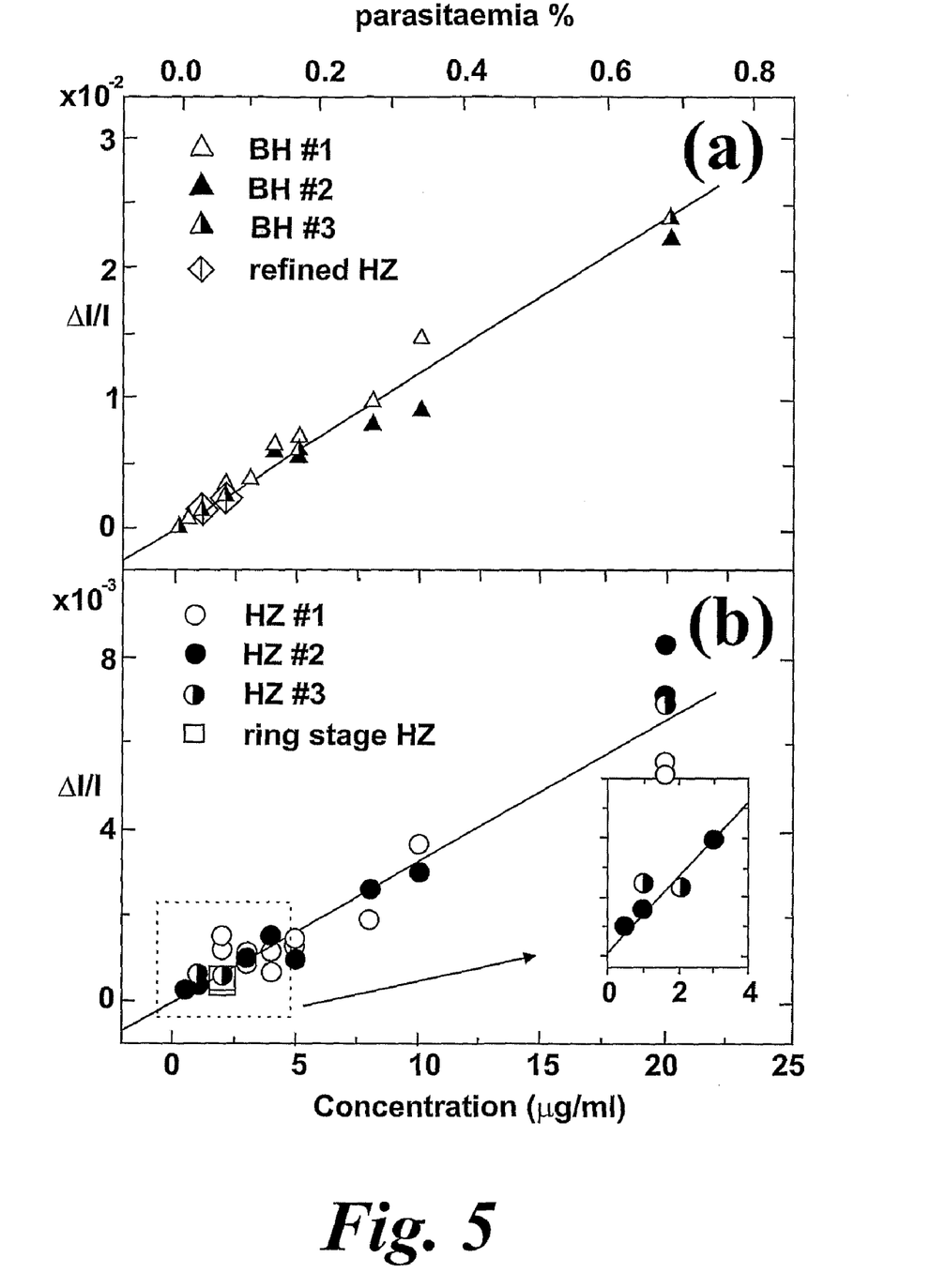

Correlation between the results shown in FIGS. 5a and 5b and malarial parasitaemia is made initially by assuming whole blood contains $5 \times 10^9$ RBCs/ml and that in mature parasitized cells conversion of 50% of the haemoglobin yields ≈0.6 pg haemozoin per cell. On this basis, detecting 100 PRBCs/µl (0.002% parasitaemia), for example, requires the measurement of haemozoin concentrations of ≈0.06 µg/ml. The lowest concentration actually measured to date is 0.1 µg/ml but as shown by the linear separation of the lower data points in FIG. 5, the resolution of the instrumentation is actually somewhat better than 0.05 µg/ml. Ultimately, the sensitivity achievable will for the most part likely be determined by the degree to which the orthogonal polarisation states used to interrogate the induced dichroism are depolarised by scattering from cellular structures and other material during their passage through the blood sample prior to interacting with haemozoin crystals. Loss of polarisation after this point is unimportant since only the resulting intensity modulation is detected.

In a confidential clinical study, the technique of the present invention was used to analyse blood samples from thirteen patients. The blood samples were all lysed and thus haemazoin originally present in red blood cells was free at the time of the measurements. The apparatus used to obtain the data shown in FIG. 5 was used to analyse the clinical blood samples. It is noted that the present invention provided a quantitative value which is related to the haemazoin load which is in turn related to the progression of the malarial parasitaemia. The clinical blood samples were also analysed using Rapid Diagnostic Tests (RDT) supplied by Orchid Biomedical Systems and Parascreen from Zephyr Biomedicals. The results are shown in Table 1, which indicates that the clinical study is 100% successful. It is considered particularly encouraging that sample #1 was correctly given a positive identification for malaria by the present invention, because in this case the infectious species was found to be Plasmodium Ovalis, which is known to be more difficult to detect.

TABLE 1

Results of clinical study.

| ID # | Patient Description | RDT diagnosis | Condition | Present Invention | ΔI/I |
|---|---|---|---|---|---|
| A | Nigerian child | P | Plasm. Falc. | P | 8.2E−5 |
| B | Nigerian child | P | Plasm. Falc. | P | 4.7E−5 |
| C | Nigerian child | P | Plasm. Falc. | P | 7.8E−5 |
| D | Nigerian child | P | Plasm. Falc. | P | 9.5E−5 |
| E | Nigerian child | P | Plasm. Falc. | P | 5.8E−5 |
| 1 | Netherlands Returned traveler | P | Plasm. Oval. | P | 4.4E−5 |
| 2 | N/A | P | Plasm. Falc. | P | 5.9E−3 |
| 3 | Tanzanian | N | Sickle cell anemia | N | — |
| 4 | Tanzanian | N | Beta-Thalassemia | N | — |
| 5 | Tanzanian | N | Genetic Disorder | N | — |
| 6 | N/A | N post dil. | — | N | — |
| 7 | N/A | inconclusive | — | N | — |
| 8 | Netherlands patient | — | N/A | N | — |

P = Positive diagnosis  N = negative diagnosis

In a further study, the fractional change in transmitted intensity was measured for suspensions of live parasitzed red blood cells grown in culture. The cell concentration in suspension was varied and for each suspension the haemazoin concentration of haemazoin was established by spectroscopy. In those experiments there was no free haemazoin external to the living cells. The instruments utilised to obtain the results shown in FIG. 5 was used to analyse the suspensions of live parasitical red blood cells, i.e., a photodetector was used to measure transmittance.

Figure 7:
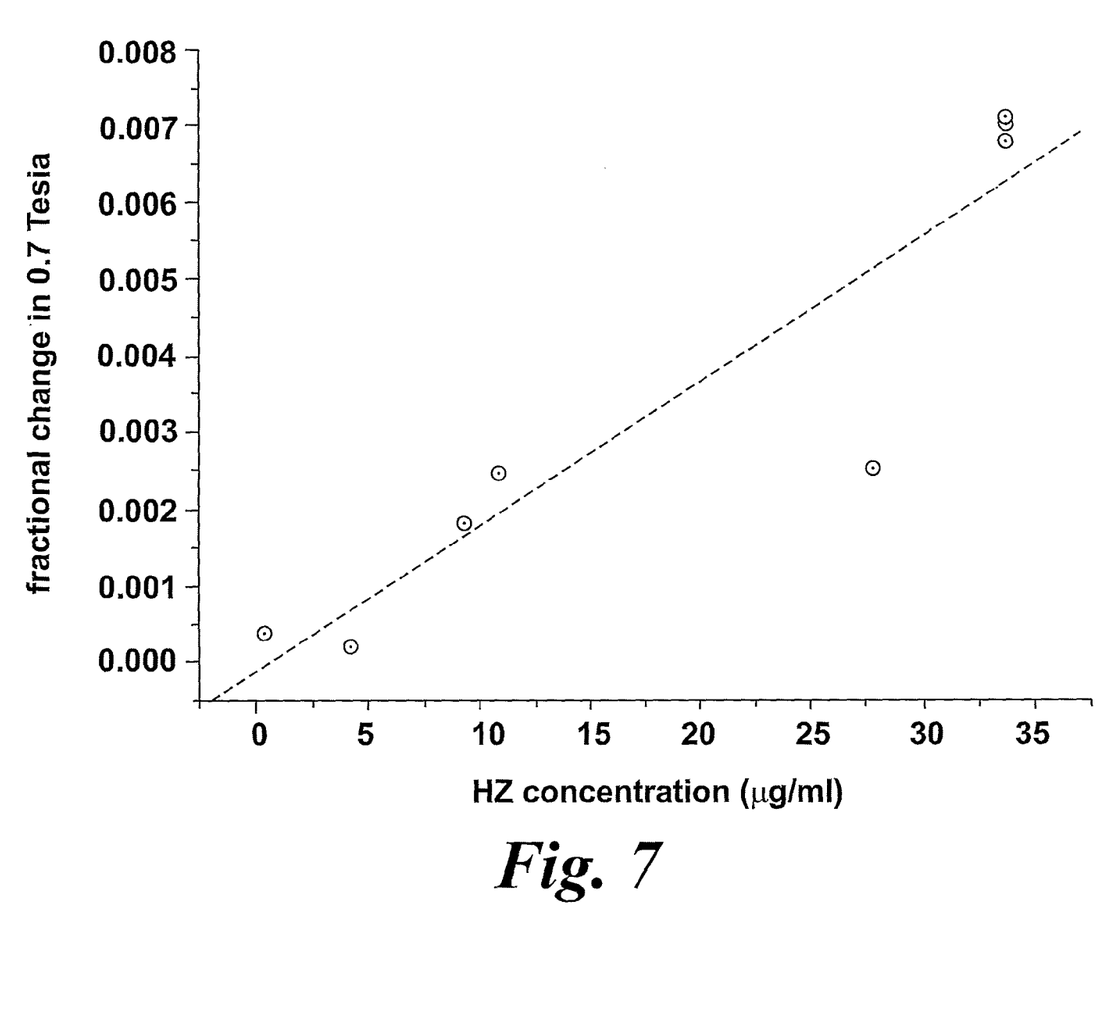
FIG. 7 shows the results of experiments measuring differential transmittance against the concentration of live parasitized red blood cells in suspension.

The results shown in FIG. 7 demonstrate conclusively that at least some of the haemazoin within the living cell vacuoles is free to respond to orientation by an applied magnetic field.

A device for in vivo measurement of malarial infection in a patient can be constructed in which measurements of peripheral tissue are made. Preferred location for making in vivo measurements are the ear lobe, a finger and a toe, although other peripheral tissue such as webbing between fingers and toes might be contemplated. It is advantageous that the testing provided by such devices is non-invasive. A device of the type generally shown in FIG. 1a, in which the magnetic field is aligned orthogonal to the incident beam and in the plane of the ear lobe, would be most preferred from the point of view of sensitivity. However, there may be merit in using the configuration shown generally in FIG. 1b, in which the magnetic field is aligned parallel to the incident beam and orthogonal to the plane of the ear lobe. In this configuration it is relatively easy to position the magnetic field production means on either side of the ear lobe. The photo-acoustic or optical transmission techniques discussed above might be employed. For applications in which the magnetic field strength is not varied, it is preferable to use a permanent magnet. In applications in which the magnetic field is varied in some way, an electromagnet might be employed, although alternatively it may be possible to use a mechanical system which employs permanent magnets, such as a system of rotating magnets. In order to provide modulation of the polarisation state of the light, it may be convenient to use two lasers which are orthogonally polarised and intensity modulated 180° out of phase and which are directed in turn to the relevant site by way of a suitable optical element such as polarising beam splitter cube.

Figure 8A:
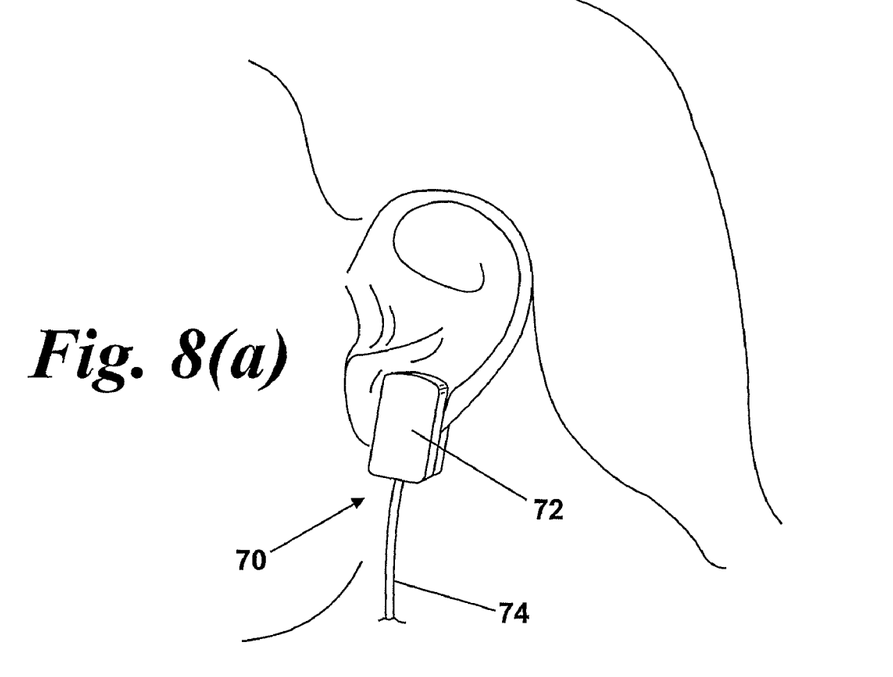
Figure 8B:
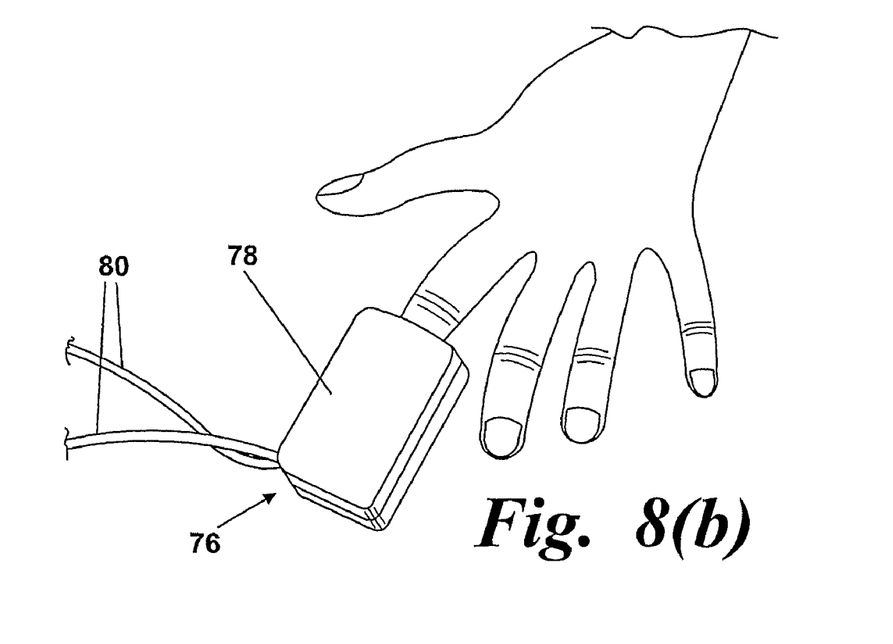

Further devices for making in vivo measurements will now be described. FIG. 8 (a) shows a device 70 for making in vivo measurements of malarial infection in a patient which clips on to the patient's earlobe. The device 70 comprises a main body 72 which houses instrumentation of the sort described herein, and a wire 74 which transmits measurement data to a suitable recording/analysis device (not shown). In place of the wire 74, a telemetric system might be used instead for these purposes. FIG. 8 (b) shows another embodiment of an in vivo device 76 which is adapted to fit onto a finger of a patient. Again, the device 76 comprises a main body 78 and wires 80, and identical comments to those made in respect of the device 70 apply to the device 76. The devices 70 and 76 may be attached to the respective body parts by any suitable means, although a clip arrangement is preferred.

It is believed that depolarisation caused by various mechanisms within the tissues of a patient can affect the working of embodiments of in vivo devices which use polarised radiation. One way in which this problem may be addressed is to utilise polarised pulsed optical fields to separate ballistic and quasi-ballistic photons from diffuse photons. Various gating techniques have been developed which can achieve this purpose (see, for example Opt. Comm. 241 (2004) 1-9, the entire contents of which are herein incorporated by reference). The delivery of the polarised light could be achieved by low birefringence spun fibres (see, for example, Optics Express 13 (10) (2005) 3841-3851, the entire contents of which are herein incorporated by reference) which will hold any polarisation state, even when the fibres are bent or twisted. Polarised laser techniques might be utilised, although alternatively special purpose LEDs as used in pulse oximetry, might be used.

Figure 9:
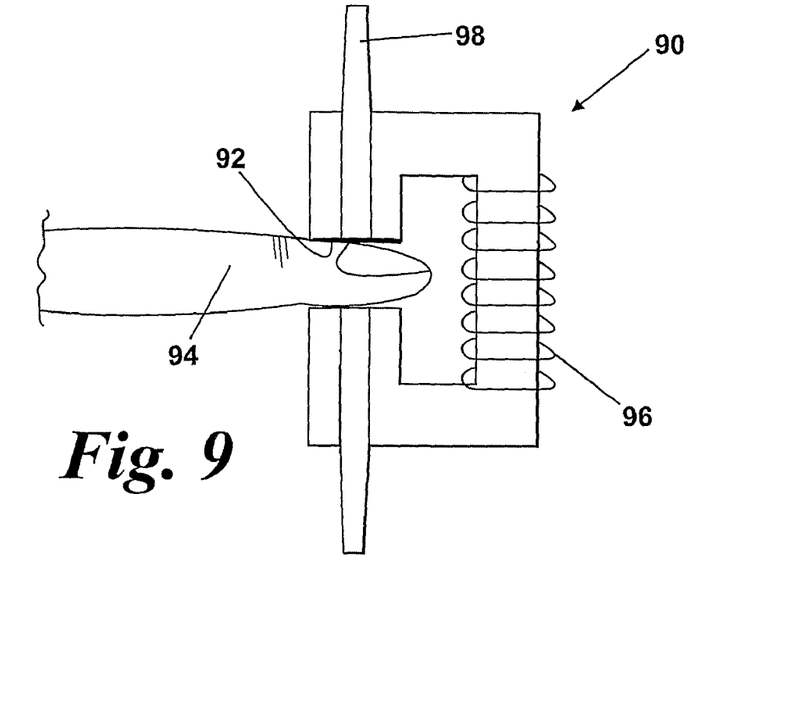
FIG. 9 shows an arrangement for performing in vivo measurements on, for example, a finger.

Alternatively, as noted above, the configuration shown generally in FIG. 1b might be utilised. FIG. 9 shows such an arrangement, depicted generally at 90. The arrangement 90 comprises a suitable aperture 92 into which a desired body part of the patient can be accommodated—in the embodiment shown in FIG. 9, a finger 94 of a patient is accommodated in the aperture 92. It should be noted that the aperture 92 may not be a permanent feature of the device but rather may be formed by clipping, clamping or otherwise positioning about the body part of the patient. The device further comprises a magnetic field production device 96 which produces a magnetic field which is transverse to the body part of the patient under investigation and parallel to a beam 98 of electromagnetic radiation. The magnetic field production device 96 has a bore formed therethrough which enables the beam 98 of electromagnetic radiation to be directed to the finger 94 of the patient. For ease of presentation the light source producing the beam of electromagnetic radiation and the detector, such as a photodetector, for measuring the transmittance of the light beam 98 through the finger 94 are not shown in FIG. 9. With the arrangement shown in FIG. 9, ie, with the magnetic field applied transverse to the interrogated body part, it is no longer necessary for the interrogating electromagnetic radiation to be polarised. Indeed, it is preferred that unpolarised electromagnetic radiation is utilised. Detection can be achieved through optical intensity modulation and/or magnetic field modulation. In either instance, an unpolarised laser or a super luminesent diode source could be used to provide the interrogating electromagnetic radiation. Optical intensity modulation can be achieved using an optical chopper or acoustic modulator to modulate the intensity of the electromagnetic radiation. Suitable means such as a locking amplifier could then be used to pick up the intensity changes from the photodetector (such as a photodiode) on the application of a DC magnetic field. Unpolarised light can be obtained when using an inherently polarised light source through the use of a depolariser or non-polarisation maintaining optical fibres.

Figure 10:
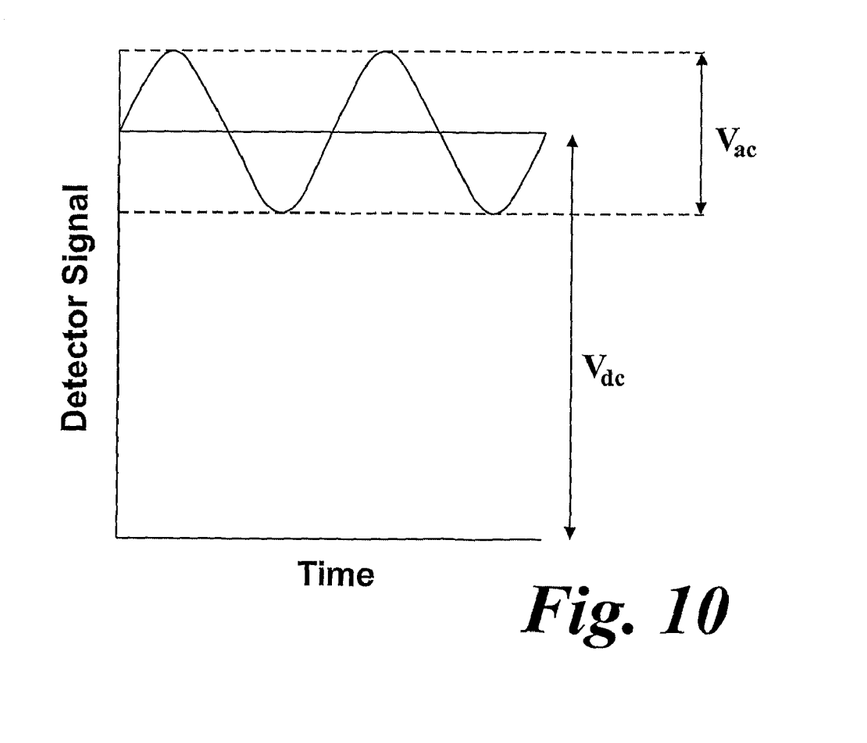
FIG. 10 shows signal levels obtained using a modulated magnetic field with the arrangement shown in FIG. 9.

Magnetic field modulation can be achieved by utilising a light beam 98 of continuous intensity, and varying the magnetic field applied across the body part of the patient. In this instance, the magnetic field production device 96 must be capable of providing a controllably variable magnetic field. The magnetic field may be modulated by imposing an ac signal onto a DC component. The AC magnetic field would produce an AC component ($V_{ac}$) in the measured transmitted light which is proportional to the change in absorption of the haemozoin caused by the magnetic field modulation. The DC magnetic field produces a DC component ($V_{dc}$) in the transmitted light measured by the photodetector. FIG. 10 shows the signal levels produced by the photodetector when using such a modulated magnetic field.

Figure 11:
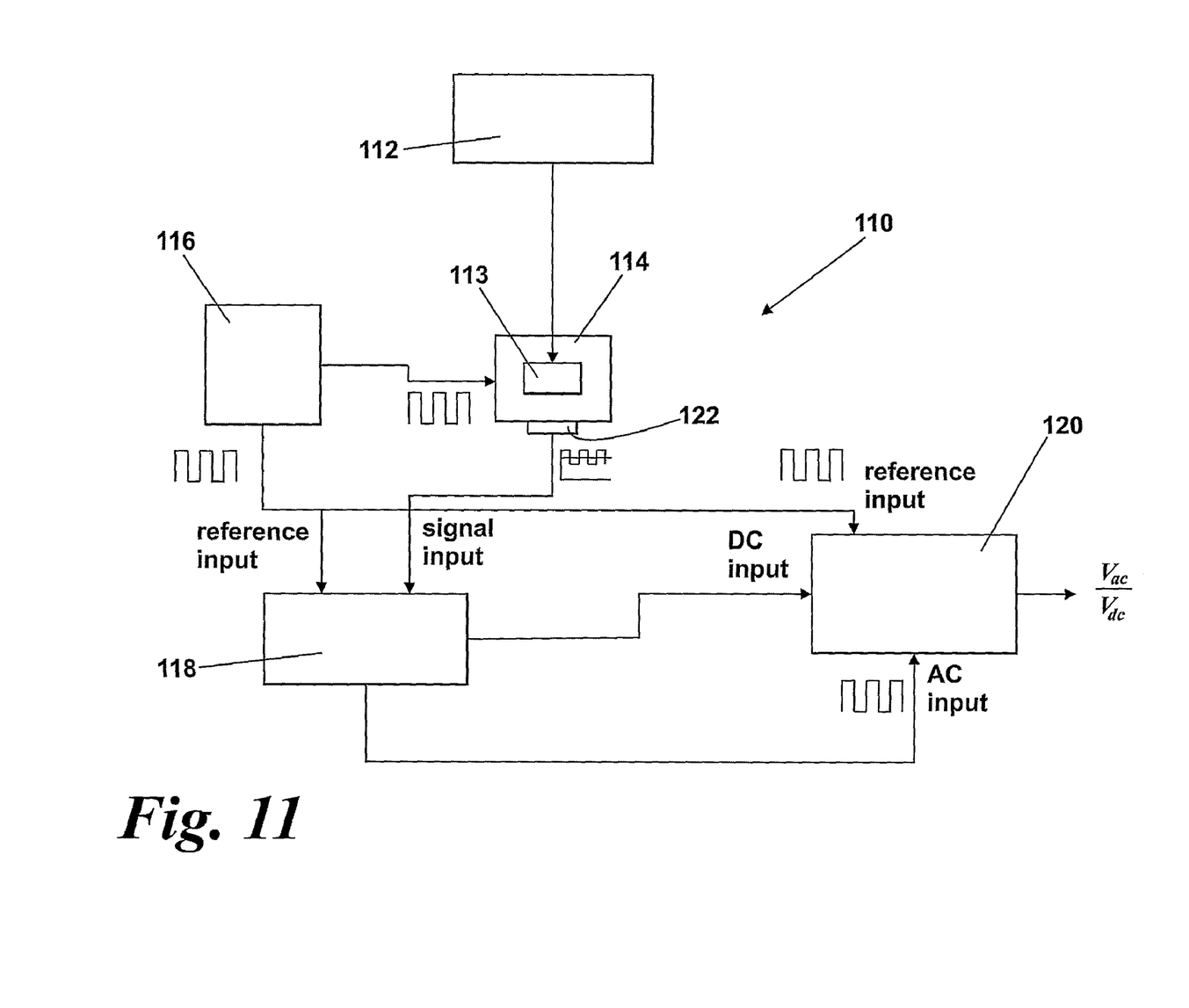
FIG. 11 is a schematic diagram of a modulated magnetic field device for making in vivo measurements.

FIG. 11 shows in schematic form an arrangement, shown generally at 110, for making in vivo measurements with unpolarised light using a modulated magnetic field which is applied transverse to the interrogated body part of a patient and parallel to an interrogating beam of electromagnetic radiation.

The arrangement comprises a light source 112, which may, for example, be a laser light source coupled to an optical fibre arrangement. The light source 112 directs electromagnetic radiation into an interrogation zone 113 which includes an electromagnetic arrangement 114 and into which a desired body part, such as a finger, can be positioned. The configuration shown in FIG. 8 might be suitable for this purpose. A magnet power source 116 controls the electromagnet 114 to produce the modulated magnetic field, and also produces a reference input which is fed into a signal processing module 118 and a lock in amplifier 120. A photodetector 122 detects electromagnetic radiation transmitted through the finger, and the signal from the photodetector 122 is fed into the signal processing module 118, which supplies a DC input and a AC input to the lock in amplifier. The output of the lock in amplifier 120 corresponds to the fractional transmittance change $V_{ac}/V_{dc}$.

At interrogation wavelengths of around 660 nm, it is necessary to modulate the magnetic field at a frequency considerably higher than that of the patient's pulse (ca. 72 beats/minutes or 1.2 Hz) to preclude interference. Alternatively, a wavelength at or around the isobestic point of 800 nm might be used, in which instance this problem would be minimised, albeit with some loss of sensitivity. Applied fields of around 0.5-0.7 T may be used. Where magnetic field modulation at low (10 Hz-20 Hz) frequency magnetic fields is used, it may be preferable to make the in vivo measurements at a peripheral location such as a finger or a toe which is relatively far removed from the head of the patient.

Figure 6:
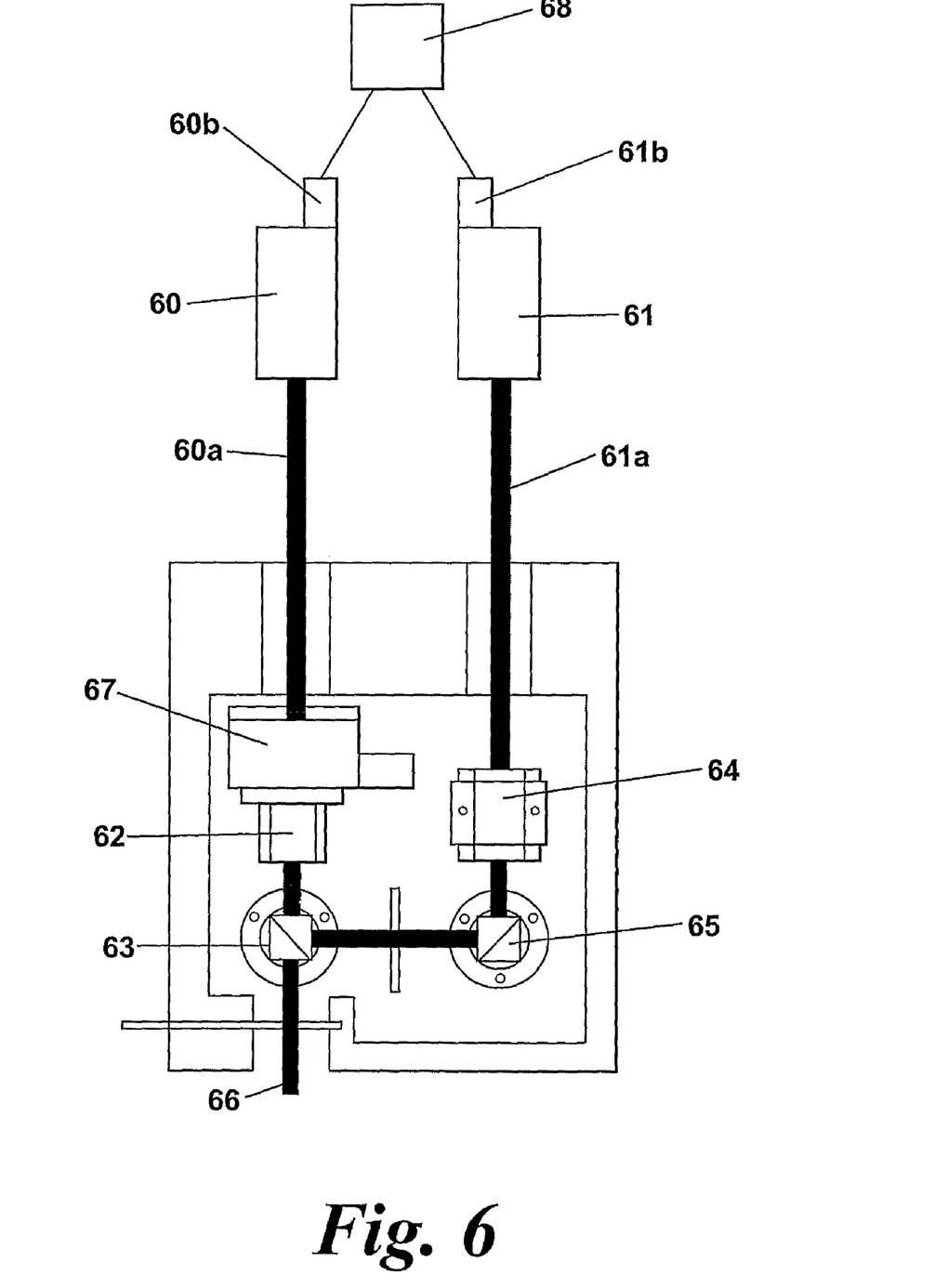
FIG. 6 is a plan view of a device for producing a polarisation modulated laser beam.

The present invention also provides an advantageous technique for achieving polarisation modulation at a pre-determined wavelength which results in a single beam of electromagnetic radiation which is alternately and controllably altered between orthogonal polarisation states. An embodiment of this aspect of the present invention is shown in FIG. 6, which depicts a first semiconductor laser 60 producing a first beam 60*a* of electromagnetic radiation and a second semiconductor laser 61 producing a second beam 61*a* of electromagnetic radiation. The first and second semiconductor lasers 60, 61 produce light of identical wavelength, although, at least in principle, differing wavelengths could be utilised. The first beam of electromagnetic radiation 60*a* passes through a Glan Taylor polariser 62 and then through a polarising beam splitter 63. The second beam 61*a* of electromagnetic radiation similarly passes through a Glan Taylor polariser 64 and is subsequently turned through 90° with a suitable polarising beam splitter 65 so as to be directed towards the polarising beam splitter 63, whereupon the first and second beams 60*a*, 61*a* of electromagnetic radiation are combined to produce a co-linear output beam 66. The linear polarisation states of the first 60*a* and second 61*a* beams are set at 90° to each other by means of the Glan Taylor polarisers 62, 64 and a micromanual rotary stage 67.

The extinction ratios of the Glan Taylor polarisers are $10^{-5}$ and the extinction ratios of the polarising beam splitters are $10^{-3}$, leading to a very high polarisation purity for each beam of $10^{-8}$. The orthogonality of the two beams is in principle only limited by the resolution of the rotary stage 67, which can be easily of the order of 15 arcsec, therefore giving an orthogonality of $90\pm4.17\times10^{-3}°$.

Each laser 60,61 has a respective laser driver 60*b*, 61*b*. Polarisation switching can be achieved by electronically modulating each laser 180° out of phase from the other using a control arrangement 68. This can be done using two out of phase digital clock signals such that the lasers are alternately switched between two adjustable intensity levels. Components such as a digital clock and digital invertors can be used to perform this function. In one specific embodiment, two circularised collimated (2 mm diameter) laser modules emitting 50 mW at 660 nm (Blue Sky Research) are driven using separate laser drivers (Micro Laser Systems), each driver providing laser power stability of >0.1% over a two hour period. Polarisation switching can be achieved by electronically modulating each laser 180° out of phase from the other at frequencies of up to 2 MHz (the frequency limit of the driver). Phase shifting can be provided by an all-pass filter or a flip flop logic circuit such that the beam exiting the optical arrangement has a constant amplitude (stability >0.2%) whilst the polarisation is switched between orthogonal states. In principle, higher switching frequencies could be obtained with different driving electronics.

All of the optical components 62, 63, 64, 65, 67 shown in FIG. 6 can be mounted on adjustable stages allowing fine adjustment of the co-linearity of the output beam 66.

The arrangement shown in FIG. 6 can be advantageously used in conjunction with the detection techniques of the present invention. In particular, the general arrangement shown in FIG. 1*a* can be used in conjunction with the device shown in FIG. 6. In this instance, a stage containing the optical components 62, 63, 64, 65, 67 can be aligned so that one state of polarisation of the output beam 66 is parallel to the direction of the applied magnetic field. The beam 66 may be expanded to a desired extent (for example to around 4-5 mm) prior to introduction to the sample by a suitable beam expander so that a large proportion of or indeed the entire sample volume is interrogated. In one embodiment, transmitted light through the sample is collected by a large area photodiode to ensure maximise light collection. A collective lens may be added.

The polarisation modulation technique described in relation to FIG. 6 is advantageously incorporated into the detection techniques of the present invention. However, the skilled reader will appreciate that the polarisation modulation provided might be advantageously utilised in other experiments and detection techniques.

The invention claimed is:

1. A method of detecting the presence of an analyte in a sample, in which the analyte is haemozoin, β-haematin or an analogous iron containing compound, the method including the steps of:
providing the sample;
applying a magnetic field across at least a portion of the sample;
detecting a physical property of the sample by introducing electromagnetic radiation into the sample and utilizing a magneto-optical spectroscopic detection technique to detect the physical property of the analyte which varies in dependence with the applied magnetic field; and
correlating the detected physical property with the presence of the analyte.

2. A method according to claim 1 in which the physical property is a property associated with the absorption of electromagnetic radiation.

3. A method according to claim 1 in which the electromagnetic radiation is in the range 400 to 700 nm.

4. A method according to claim 3 in which the electromagnetic radiation is greater than 600 nm.

5. A method according to claim 1 in which the electromagnetic radiation is polarised.

6. A method according to claim 5 in which the polarisation state of the electromagnetic radiation is varied, and the presence of the analyte is detected by detecting a dependence of the detected physical property on the polarisation state.

7. A method according to claim 1 in which the transmission of the electromagnetic radiation through the sample is detected.

8. A method according to claim 1 in which the magnitude and/or the direction of the applied magnetic field is varied, and the presence of the analyte is detected by detecting a dependence of the detected physical property on the variation of the applied magnetic field.

9. A method of detecting the presence of malarial parasites in a blood containing sample including the steps of:
detecting the presence of haemozoin in the blood containing sample by a detection technique which is substantially unaffected by the presence of other constituents of the blood;
correlating the presence of haemozoin with the presence of malarial parasites in the blood containing sample;
in which the step of detecting the presence of haemozoin is performed by applying a magnetic field across at least a portion of the blood containing sample and detecting a physical property of the blood containing sample by introducing electromagnetic radiation into the sample and utilizing a magneto-optical spectroscopic detection technique to detect the physical property of haemozoin which varies in dependence with the applied magnetic field.

10. A device for detecting the presence of an analyte in a sample, in which the analyte is haemozoin, β-haematin or an analogous iron containing compound, the device including:
magnetic field applying means for applying a magnetic field across at least a portion of the sample;
detection means for detecting a physical property of the sample by introducing electromagnetic radiation into the sample and utilizing a magneto-optical spectroscopic detection technique to detect the physical property of the analyte which varies in dependence with the applied magnetic field; and correlation means for correlating the detected physical property with the presence of the analyte.

11. A device for detecting the presence of malarial parasites in a blood containing sample including:
    means for detecting the presence of haemozoin in the blood containing sample, the detection being substantially unaffected by the presence of other constituents of the blood; and
    means for correlating the presence of haemozoin with the presence of malarial parasites in the blood containing sample;
    in which the means for detecting the presence of haemozoin includes magnetic field applying means for applying a magnetic field across at least a portion of the sample; and
    detection means for detecting a physical property of the sample by introducing electromagnetic radiation into the sample and utilizing a magneto-optical spectroscopic detection technique to detect the physical property of haemozoin which varies in dependence with the applied magnetic field.

12. A device according to claim 11 in which the magnetic field applying means is controllable so as to vary the magnitude and/or the direction of the applied magnetic field.

13. A device according to claim 11 in which the detection means includes means for providing electromagnetic radiation and sensing means for detecting a physical property associated with the absorption of the electromagnetic radiation by haemozoin, wherein the device is configured so that the electromagnetic radiation propagates into the sample along an axis, and the magnetic field applying means applies a magnetic field which is aligned in parallel with said axis of propagation.

14. A device according to claim 11 in which the detection means includes means for providing electromagnetic radiation and sensing means for detecting a physical property associated with the absorption of the electromagnetic radiation by haemozoin, wherein the device is configured so that the electromagnetic radiation propagates into the sample along an axis, and the magnetic field applying means applies a magnetic field which is aligned orthogonal to said axis of propagation.

15. A device according to claim 11 which is attachable to peripheral tissue of a patient, and in which the means for detecting the presence of haemozoin performs in vivo detection of the presence of haemozoin in the bloodstream of the patient.

16. A method of detecting the presence of an analyte in a sample, in which the analyte is haemozoin, β-haematin or an analogous iron containing compound, the method including the steps of:
    providing the sample;
    applying a magnetic field across at least a portion of the sample;
    detecting a physical property of the sample by introducing electromagnetic radiation into the sample, the detected physical property corresponding to the physical property of the analyte which varies in dependence with the applied magnetic field and is associated with the absorption of electromagnetic radiation; and
    correlating the detected physical property with the presence of the analyte.

17. A method of detecting the presence of malarial parasites in a blood containing sample including the steps of:
    detecting the presence of haemozoin in the blood containing sample by a detection technique which is substantially unaffected by the presence of other constituents of the blood;
    correlating the presence of haemozoin with the presence of malarial parasites in the blood containing sample;
    in which the step of detecting the presence of haemozoin is performed by applying a magnetic field across at least a portion of the blood containing sample and detecting a physical property of the blood containing sample by introducing electromagnetic radiation into the sample, the detected physical property corresponding to the physical property of haemozoin which varies in dependence with the applied magnetic field and is associated with the absorption of electromagnetic radiation.

18. A device for detecting the presence of an analyte in a sample, in which the analyte is haemozoin, β-haematin or an analogous iron containing compound, the device including:
    magnetic field applying means for applying a magnetic field across at least a portion of the sample;
    detection means for detecting a physical property of the sample by introducing electromagnetic radiation into the sample, the detected physical property corresponding to the physical property of the analyte which varies in dependence with the applied magnetic field and is associated with the absorption of electromagnetic radiation; and
    correlation means for correlating the detected physical property with the presence of the analyte.

19. A device for detecting the presence of malarial parasites in a blood containing sample including:
    means for detecting the presence of haemozoin in the blood containing sample, the detection being substantially unaffected by the presence of other constituents of the blood; and
    means for correlating the presence of haemozoin with the presence of malarial parasites in the blood containing sample;
    in which the means for detecting the presence of haemozoin includes magnetic field applying means for applying a magnetic field across at least a portion of the sample and
    detection means for detecting a physical property of the sample by introducing electromagnetic radiation into the sample, the detected physical property corresponding to the physical property of haemozoin which varies in dependence with the applied magnetic field and is associated with the absorption of electromagnetic radiation.

* * * * *